(12) United States Patent
Weisshaupt et al.

(10) Patent No.: US 9,033,251 B2
(45) Date of Patent: May 19, 2015

(54) RFID TAG

(71) Applicant: Aesculap AG, Tuttlingen (DE)

(72) Inventors: Dieter Weisshaupt, Immendingen (DE); Pedro Morales, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 14/141,592

(22) Filed: Dec. 27, 2013

(65) Prior Publication Data

US 2014/0131454 A1 May 15, 2014

Related U.S. Application Data

(63) Continuation of application No. PCT/EP2012/065324, filed on Aug. 6, 2012.

(30) Foreign Application Priority Data

Aug. 8, 2011 (DE) .................. 10 2011 052 501

(51) Int. Cl.
*G06K 19/06* (2006.01)
*G06K 19/077* (2006.01)
*A61B 19/00* (2006.01)
*A61B 17/28* (2006.01)
*A61B 17/3201* (2006.01)
*A61B 17/3211* (2006.01)

(52) U.S. Cl.
CPC ....... *G06K 19/07758* (2013.01); *A61B 17/2812* (2013.01); *A61B 17/3201* (2013.01); *A61B 17/3211* (2013.01); *A61B 19/44* (2013.01); *G06K 19/07771* (2013.01); *A61B 2019/448* (2013.01)

(58) Field of Classification Search
CPC .................. G06K 19/07749; G06K 19/0775; G06K 19/06; G06K 19/00; G06K 7/08; G06K 5/00
USPC .......................... 235/492, 380, 451, 375, 487
See application file for complete search history.

(56) References Cited

U.S. PATENT DOCUMENTS

| 8,461,992 | B2 * | 6/2013 | Westrick et al. ........... 340/572.1 |
| 2006/0038683 | A1 * | 2/2006 | Claessens et al. ......... 340/572.1 |

(Continued)

FOREIGN PATENT DOCUMENTS

| DE | 10 2006 029 1 | 12/2007 |
| DE | 10 2006 029 122 | 12/2007 |

(Continued)

*Primary Examiner* — Edwyn Labaze
(74) *Attorney, Agent, or Firm* — Lipsitz & McAllister, LLC

(57) ABSTRACT

An RFID tag is provided that is suitable for mounting on surgical instruments, and by means of which stable anchoring on the instrument, encapsulation of the RFID elements from the surroundings, good cleanability and improved detectability can be achieved. The RFID tag has a metal holder, a housing that is made of an electrically non-conductive or slightly conductive material, an accommodating chamber and an RFID element with an antenna. The RFID element is arranged in the accommodating chamber of the housing. The housing has a first end which is held on the metal holder. The accommodating chamber in the housing is formed to be spatially spaced apart from the first end of the housing. The RFID element is positioned in the accommodating chamber in such a way that the antenna of the RFID element is spatially arranged substantially outside of the metal holder.

24 Claims, 5 Drawing Sheets

(56) References Cited

U.S. PATENT DOCUMENTS

| | | |
|---|---|---|
| 2006/0084934 A1 | 4/2006 | Frank |
| 2006/0174470 A1* | 8/2006 | Sadek ............................ 29/592.1 |
| 2009/0277959 A1* | 11/2009 | Grimard ......................... 235/380 |
| 2009/0281419 A1 | 11/2009 | Troesken et al. |
| 2010/0026456 A1 | 2/2010 | Cline et al. |
| 2010/0219252 A1* | 9/2010 | Kikuchi et al. ................ 235/488 |
| 2010/0272532 A1 | 10/2010 | Hegedus et al. |
| 2011/0057854 A1 | 3/2011 | Elbinger et al. |
| 2012/0048947 A1* | 3/2012 | Kube et al. ..................... 235/492 |
| 2012/0187197 A1* | 7/2012 | Masin ............................ 235/492 |
| 2013/0048947 A1* | 2/2013 | Grimes et al. ................... 257/15 |
| 2013/0199026 A1* | 8/2013 | Mazoki et al. ................... 29/601 |

FOREIGN PATENT DOCUMENTS

| | | |
|---|---|---|
| JP | 2007183840 | 7/2007 |
| JP | 2011502677 | 1/2011 |
| WO | WO 2006/020377 | 2/2006 |
| WO | WO 2008/112709 | 9/2008 |
| WO | 2009063323 | 5/2009 |
| WO | 2009100729 | 8/2009 |
| WO | WO 2010/145651 | 12/2010 |

* cited by examiner

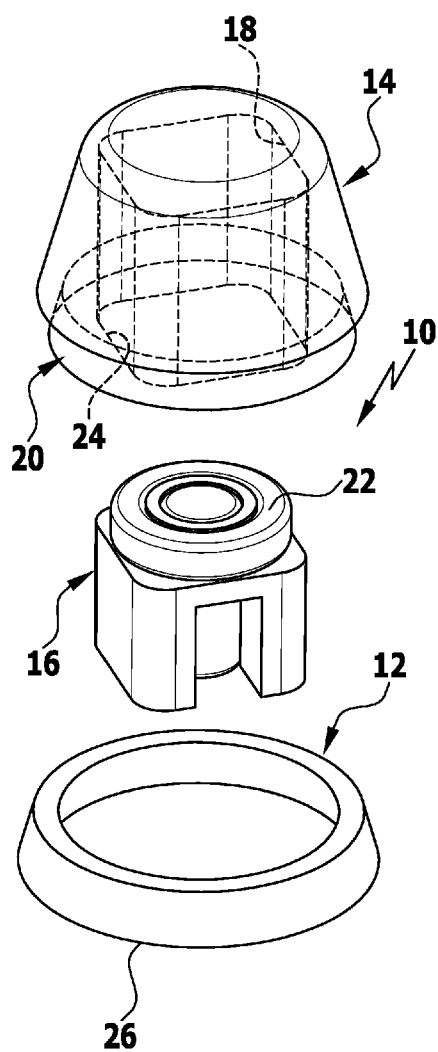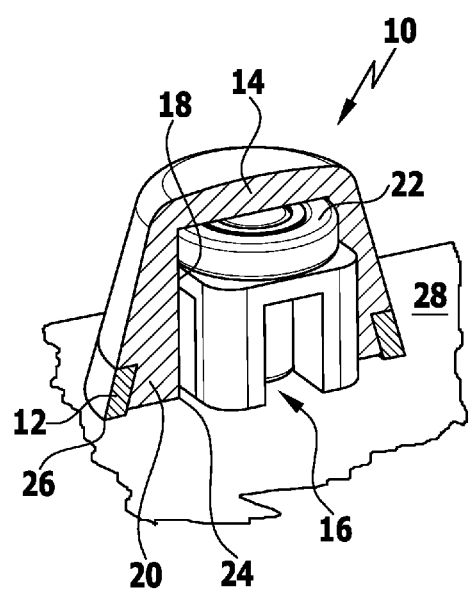
FIG.1A
FIG.1B

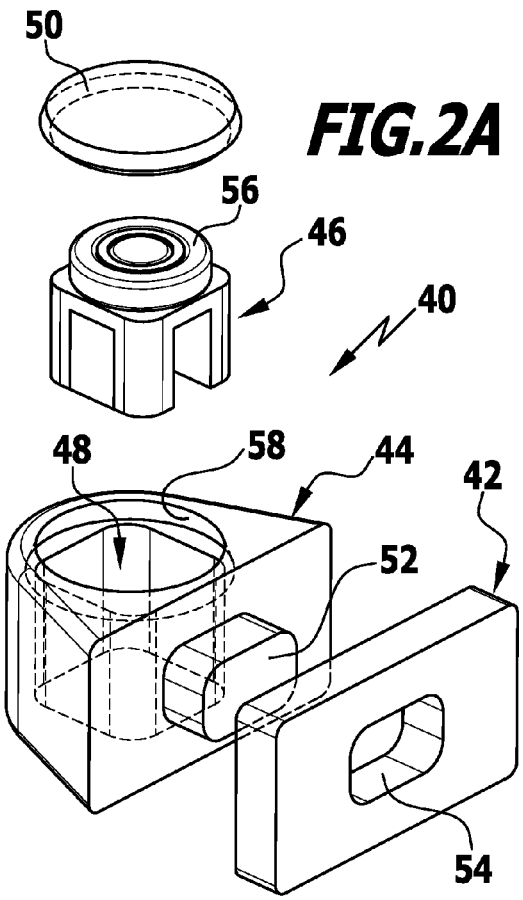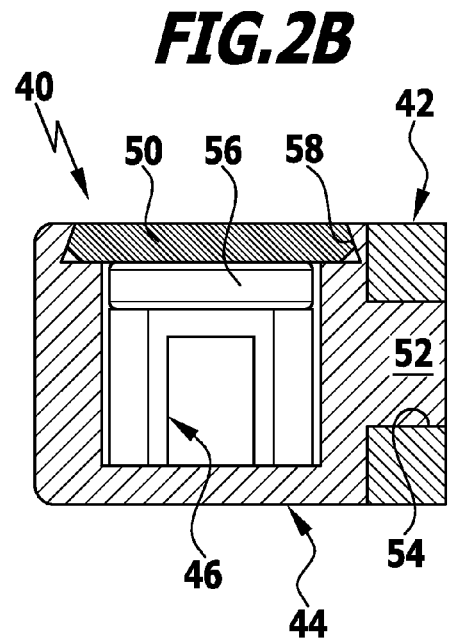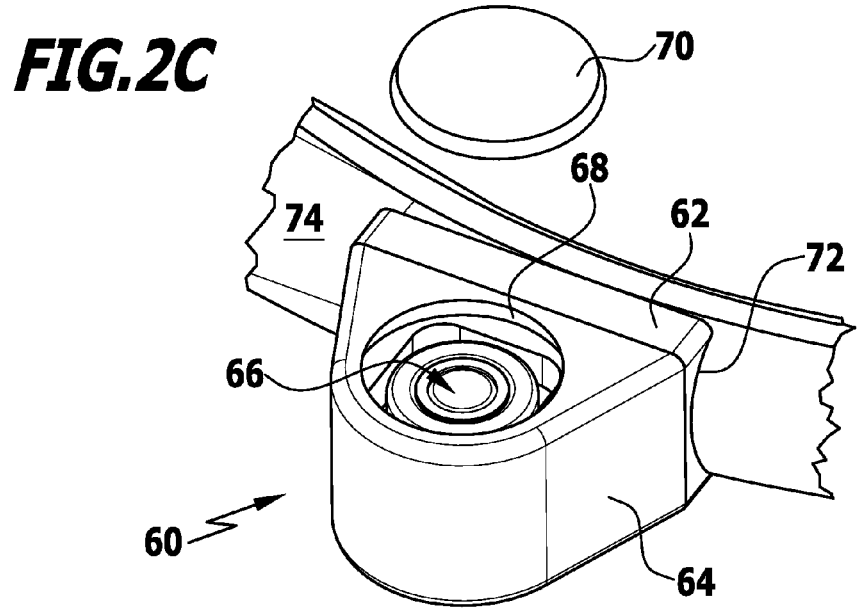

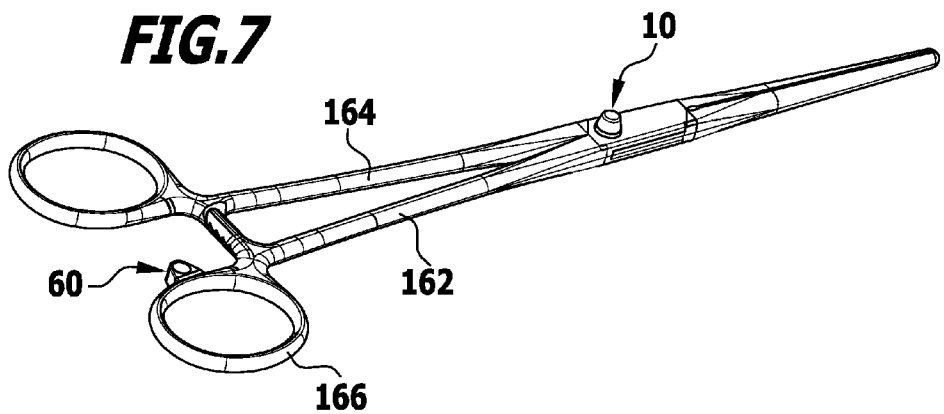
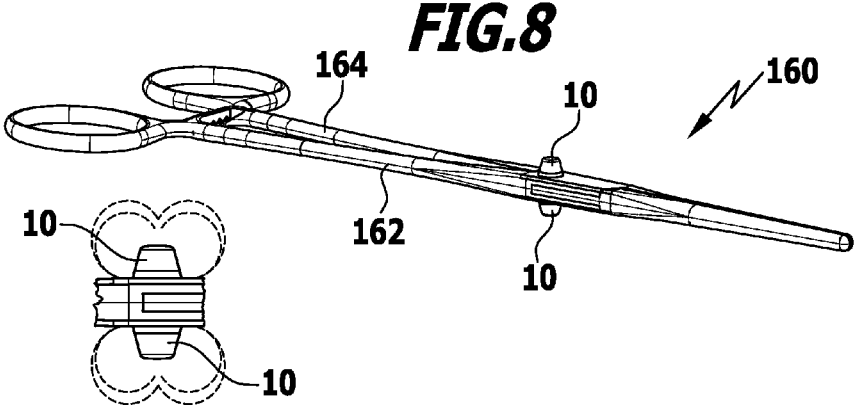
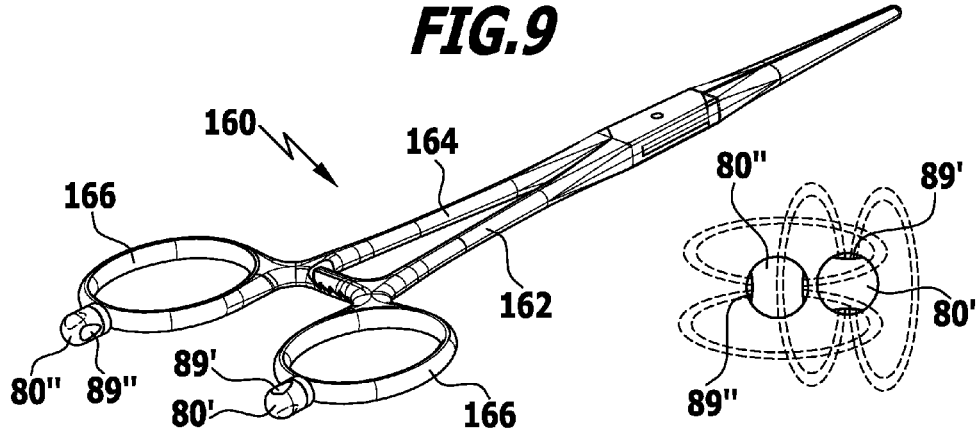

RFID TAG

This application is a continuation of international application number PCT/EP2012/065324 filed on Aug. 6, 2012 and claims the benefit of German application number 10 2011 052 501.7 filed on Aug. 8, 2011, which are incorporated herein by reference in their entirety and for all purposes.

BACKGROUND OF THE INVENTION

The invention relates to an RFID marking element for mounting on surgical instruments, hereinafter referred to as "tag" for short.

Conventional RFID tags for mounting on surgical instruments comprise, in addition to a substantially annular metal holder, a disc-shaped plastics or ceramic body that is surrounded by the metal holder. The metal holder itself can be secured by welding, in particular laser welding, to an instrument on which a tag is to be mounted.

In other solutions, an RFID element is potted in a hole in the instrument.

The advantages of surgical instruments on which RFID tags are mounted are their easy identifiability and traceability, it being possible to check and read the RFID tags without particular skills on the part of the personnel.

Instruments having RFID tags mounted thereon reduce the risk that instruments remain in the body of the patient after surgery. In addition, it is easier to manage the inventory of instruments and to better track the use of the surgical instruments during their service life.

The two known solutions have the problem that the transmitting power of the RFID element of the RFID tag is comparatively low.

In the case of RFID tags known under the name SIMSAFE, an annular metal holder is used in which a slot is provided so as to prevent a short circuit. Nevertheless, the transmitting power of RFID tags mounted in this manner on instruments is still too low for simple handling in everyday hospital routines.

It is an object of the invention to propose an RFID tag that is suitable for mounting on surgical instruments, and by means of which, in addition to stable anchoring on the instrument, encapsulation of the RFID elements from the surroundings, good cleanability, and improved detectability, i.e, transmitting power in the surrounding area of the instrument, can also be achieved.

SUMMARY OF THE INVENTION

According to the invention, this object is achieved by an RFID tag as defined in claim 1.

Unlike the RFID tags known heretofore, the RFID tags according to the invention are provided with a housing which is held only at a first end on the metal holder. The accommodating chamber for the RFID element is formed in the housing to be spatially spaced apart from the first end of the housing. This enables an arrangement of the RFID element with its antenna in such a manner that the antenna is spatially arranged substantially outside of the metal holder. The antenna is preferably arranged in the housing in such a manner that a spatial distance from the metal holder results.

In addition to stable anchoring of the tag on the instrument, the RFID tags according to the invention enable secure encapsulation, good cleanability, as well as a positioning of the RFID element in the housing which allows unhindered emission from the RFID element.

Furthermore, a high level of flexibility is provided in terms of the selection of the location on the instrument where the RFID tag is to be positioned.

The housing including its accommodating chamber can be implemented as a simple encapsulation, the RFID element being moulded into the housing material. A separate production step for forming the accommodating chamber is not necessary in this embodiment.

DETAILED DESCRIPTION OF THE INVENTION

Preferred materials for producing the housing or the encapsulation are plastics or ceramic materials.

The RFID elements are preferably inserted into a previously-produced accommodating chamber of the housing and are retained there and connected to the housing, for example in a force-fit and/or positive-fit manner or in an integrally bonded manner.

According to a preferred variant of the RFID tag according to the invention, a housing that is open on one side is provided as the housing, the opening of the housing forming an access to the accommodating chamber. The opening is configured such that the RFID tag can be easily inserted into the housing or the accommodating chamber thereof. The cross-section of the accommodating chamber is preferably adapted to the geometry of the RFID element in such a manner that the RFID element, guided by the walls of the chamber, can be pressed into its final assembly position.

The accommodating chamber as a chamber that is open on one side is closable by a closure element, the closure element preferably being glued or welded to the housing, in particular welded by means of ultrasound.

In an alternative preferred embodiment of the invention, the first end of the housing comprises the opening that forms the access to the accommodating chamber. The metal holder can be configured such that the first end, which comprises the opening forming the access to the accommodating chamber, is completely accommodated there. By subsequently welding the metal holder to the surgical instrument, a tight connection between the metal holder and the surgical instrument can be established so that the accommodating chamber of the housing can remain open toward the opening. The metal holder and its connection to the surgical instrument form sufficient protection against environmental influences, in particular also during sterilization of the instruments.

Preferably, the RFID element is arranged with its antenna facing away from the metal holder and/or is arranged in the accommodating chamber to be spatially spaced apart from the metal holder.

The connection between the housing and the metal holder can be implemented in different variations. In one variant, the housing is injection-molded onto the metal holder. In particular plastics materials are suitable for producing the housing.

On the other hand, the metal holder may also be injection-molded onto the housing, in which case the housing is preferably formed from ceramic material.

As a further alternative, the housing made of plastics or ceramic materials can be held on the metal holder in a force-fit and/or positive-fit manner, in particular also by a press fit.

Lastly, gluing the housing to the metal holder is also possible, optionally while simultaneously closing the opening which forms an access to the accommodating chamber.

The housing of the RFID tag preferably has a substantially flat surface region which has a predefined orientation relative to the antenna of the RFID element, the orientation preferably being selected to be approximately coplanar with the antenna plane of the RFID element. In this manner, placing and orienting the RFID tag on the instrument can be carried out more correctly when the housing has already been closed.

The invention further relates to an instrument on which an RFID tag according to the present invention is mounted.

It is preferred in particular for the metal holder of the RFID tag to be welded to the instrument, laser welding being particularly preferred here.

In the case of further preferred instruments according to the invention, two or more RFID tags are mounted on the instrument, the two or more RFID tags being arranged on the instrument in such a manner that the antennas of their respective RFID elements are aligned in different planes, the planes preferably forming an angle of approximately 70° to approximately 110°, preferably approximately 90°, with one another.

Using two or more RFID tags on an instrument allows simpler and more secure identification of the instrument in a group together with other instruments.

In a particularly preferred embodiment of the RFID tag according to the invention, two RFID elements with antennas having a substantially orthogonal alignment with respect to one another are arranged in a common housing. Here, identifying the instrument independent of its position can then be carried out with only one RFID tag.

With the RFID tag designed according to the invention, it is in particular possible to secure the tags on the instrument itself without modifying the instrument; in particular, no component on the instrument has to be spot-drilled or otherwise modified in order to accommodate the RFID tag.

In the prior art, this often leads to strength problems and, moreover, such a modification on the instrument itself can result in the instrument losing its certification, in particular if the hole is not defined in the original production documentation of the instrument, i.e, if the instrument is retroactively equipped.

This shows that the RFID tags according to the invention can advantageously also be used in particular when conventional instruments, which were not developed from the outset for mounting RFID tags thereon, are to be made identifiable and traceable via RFID tags.

Moreover, the RFID tags of the present invention are producible in a simple manner with a high level of seal-tightness and can be securely attached on the instrument, with good cleanability, good function and high flexibility in selecting the mounting location of the tags on the instruments being provided.

These and other advantages of the present invention are explained in greater detail below with reference to the drawings.

BRIEF DESCRIPTION OF THE DRAWINGS

FIG. 1A shows an exploded view of a first embodiment of an RFID tag according to the invention;

FIG. 1B shows a sectional drawing of the assembled RFID tag of the first embodiment in FIG. 1A;

FIG. 2A shows an exploded view of a second embodiment of the RFID tag according to the invention;

FIG. 2B shows a sectional drawing of the assembled RFID tag in FIG. 2A;

FIG. 2C shows the RFID tag in FIG. 2A, held on a surgical instrument;

FIG. 7 shows a further surgical instrument having two RFID tags according to the invention as shown in FIGS. 1A and 2C;

FIG. 8 shows a further surgical instrument having two RFID tags according to FIG. 1A mounted thereon; and FIG. 9 shows a further surgical instrument having an RFID tag according to FIG. 3A mounted thereon.

DETAILED DESCRIPTION OF THE DRAWINGS

Figure 3A:
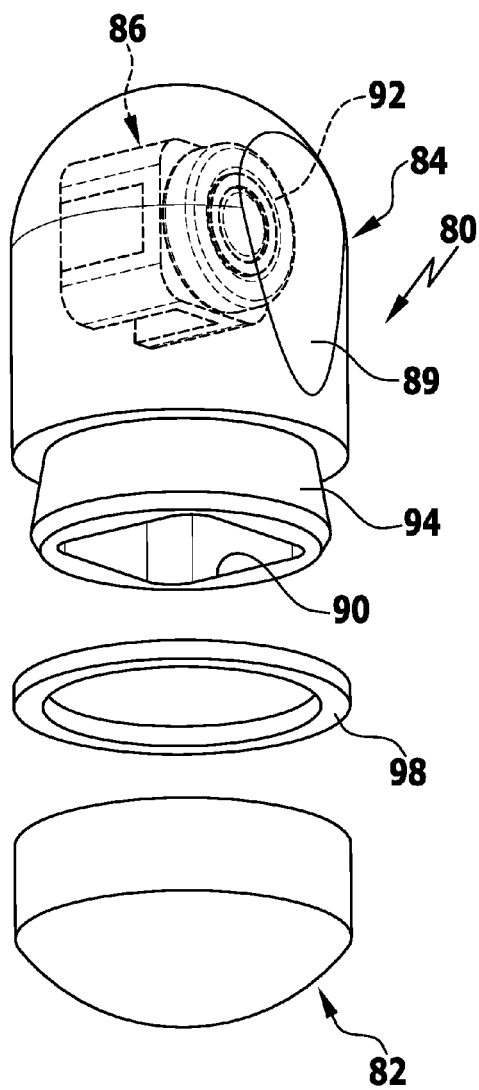
FIG. 3A shows an exploded view of a third embodiment of an RFID tag according to the invention.

FIG. 1 shows an RFID tag of the present invention, designated as a whole by reference number 10, comprising an annular metal holder 12, a housing 14, and an RFID element 16 to be arranged in the housing.

The housing 14 has an accommodating chamber 18 in which the RFID element 16 is accommodated.

The housing 14 also has a truncated cone-shaped outer contour with an edge 20 which is recessed at the lower end of the truncated cone and which can be inserted in a press fit into the complementarily shaped opening of the annular metal holder 12. The latter is possible if the housing 14 is made of plastics. Alternatively, the metal ring 12 can also be injection-molded onto the housing 14, which in this case is made from a ceramic material, for example.

Moreover, the first end of the housing 14 having the recessed edge 20 also has an opening 24 that provides access to the accommodating chamber 18 of the housing 14.

The accommodating chamber 18 and the opening 24 of the housing 14 are adapted to the geometry of the RFID element 16 so that the latter can be placed in the accommodating chamber 18 in a guided manner and with a predefined spatial orientation.

The RFID element 16 is preferably inserted into the accommodating chamber 18 in such a manner that in the assembled state of the RFID tag 10, the antenna 22 of the RFID element, in FIG. 1A on top, is spatially spaced apart from the annular metal holder 12 and is in particular arranged facing away from the metal holder. The recessed edge 20 of the housing 14 forms a first end thereof, by means of which the housing is held in the annular metal holder 12.

The RFID element 16 is secured in the accommodating chamber 18 either in a form-fit and/or positive-fit manner, or in an integrally bonded manner by means of an adhesive, in particular an adhesive based on silicone material. As an alternative, the plastics housing 14 may be injection-molded from a plastics material onto the RFID element 16 in the shown mutual orientation.

The first end of the housing 14 with its opening 24 can remain open in the assembled state of the RFID tag 10, since the RFID tag is subsequently held with the lower edge 26 of the annular metal holder 12 on a surgical instrument, preferably via a circumferentially extending laser weld, so that the RFID element 16 is sufficiently protected against environmental influences.

FIG. 1B shows a sectional drawing of the RFID tag 10 in the assembled state, an instrument surface 28 also being schematically illustrated for clarifying the mounting of the RFID tag 10 on an instrument.

FIG. 2A shows in an exploded view a second embodiment of an RFID tag 40 according to the invention, comprising a metal holder 42 that is rectangularly formed here, a housing 44 having a parabolic cross-section, and an RFID element 46.

The housing 44 has an accommodating chamber 48 which is open on one side and which in turn is adapted to the shape of the RFID element 46. With the RFID element 46 inserted, the accommodating chamber 48 that is open on one side can be sealingly closed by means of a closure or cover element 50, for example by gluing or welding, in particular with an adhesive made of a plastics material.

The axis of symmetry of the accommodating chamber 48 is aligned to be perpendicular to the parabola plane of the housing.

The housing 44, which is parabolic in cross-section, has at its first end a pin-shaped projection 52 that can engage in an opening 54 of the metal holder 42 and can be fixed in a form-fit and/or positive-fit manner, or can be fixed in an integrally bonded manner, for example by means of a silicone material.

The RFID element 46 is once again equipped with an antenna 56 which, in the mounted state of the RFID element in the housing 44, is spatially spaced apart from the metal holder 42.

FIG. 2B shows the RFID tag 40 according to the invention in the assembled state, it being apparent from the sectional drawing in FIG. 2B that the cover or closure element 50, due to the complementary formation of its edge region, can be inserted in a form-fit manner into an opening 58 of the housing 44. When the materials are appropriately selected, the cover 50 and the housing can be welded together, in particular by means of ultrasound, or glued together.

In the exemplary embodiment shown in FIGS. 2A and 2B, the RFID element 46 is completely encapsulated in the housing 44 and is thus protected against environmental influences, in particular also during sterilization of an instrument equipped in this way.

FIG. 2B clearly shows again the spatial distance of the antenna 56 of the RFID element 46 from the metal holder 42, which is a requirement for the significantly improved transmitting power of the RFID tag 40 according to the invention.

FIG. 2C illustrates a variant of the RFID tag 40 as RFID tag 60, comprising a metal holder 62, a housing 64 and an RFID element 66 accommodated in the housing 64. The opening 68 that is present in the housing 64 on one side is still open here, and a cover element 70 is provided so as to close the opening 68 and thus encapsulate the RFID element 66.

Furthermore, FIG. 2C shows an adaptation of the surface 72 of the metal holder 62 opposite from the housing 64, having a concave design so as to engage in a form-fit manner with a convex surface 74 of a surgical instrument and then to be connected thereto, for example by means of laser welding.

FIG. 3A shows a further embodiment of an RFID tag 80 according to the invention, comprising a metal holder 82, a housing 84 and an RFID element 86 arranged in the housing.

For accommodating the RFID element 86, the housing 84, which is substantially cylindrical, has an accommodating chamber 88 that extends parallel to the cylinder axis of the housing 84. The housing 84 has an opening 90 that provides access to the accommodating chamber 88 and through which the RFID element 86 can be inserted into the accommodating chamber 88.

Figure 3B:
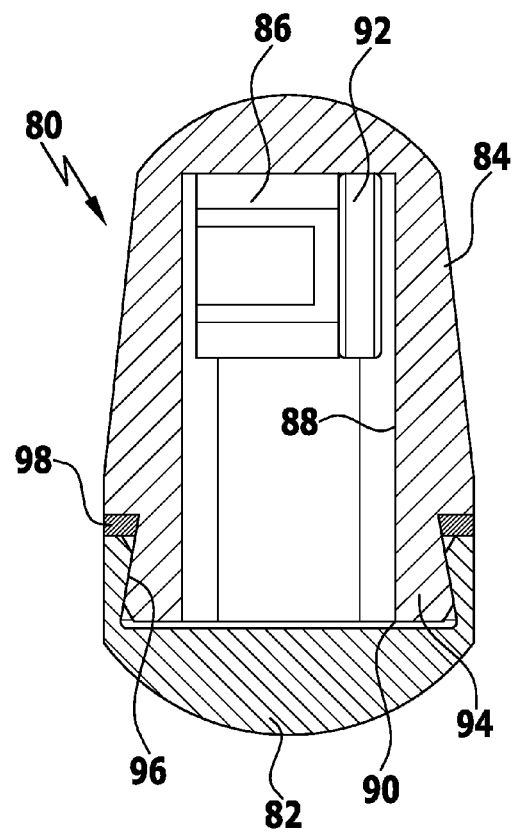
FIG. 3B shows a sectional view of the assembled RFID tag in FIG. 3A.

The RFID element 86 can be fixed in the accommodating chamber 88, for example by adhesive bonding in its position at the first end, i.e. the end opposite from the opening 90, as illustrated in the FIGS. 3A and 3B.

In this manner, the antenna 92 of the RFID element 86 is spatially kept outside of the metal holder 82, and overall is clearly spaced apart therefrom so that the transmitting power of the RFID element 86 is not impaired.

A substantially planar surface region 89 of the housing is oriented coplanar with respect to the position of the RFID element 86 with its antenna 92, so that even in the closed state of the RFID tag 80 the orientation of the antenna 92 is still discernible.

A recessed conical structure element 94 is arranged at the first end of the housing 84 that has the opening 90, and can engage in a corresponding recess 96 in the metal holder 82 which is formed as a blind hole.

For sealing between the metal holder 82 and the housing 84, a sealing element 98 is arranged, which, due to the conical structure of the free end 94 and the opening 96 of the metal holder 82, which in the present case is a blind hole opening, is clamped in between so that a sealing connection between the housing 84 and the metal holder 82 is formed. Here as well, the RFID element 86 is once again sufficiently protected against environmental influences.

As in the case of the previously described RFID tag according to the invention, the RFID tag 80 with its metal holder 82 can also be welded to an instrument, and an appropriate corresponding instrument can be thus equipped.

Figure 4:
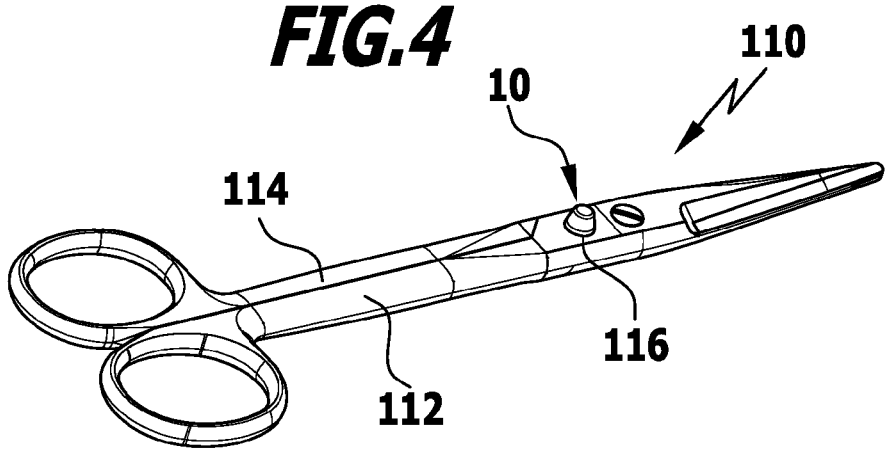
FIG. 4 shows a surgical instrument having an RFID tag according to the invention as shown in FIG. 1A.

FIG. 4 shows an instrument in the form of scissors 110 as an example of the mounting of the RFID tag 10 of FIG. 1A on a surgical instrument. Here, the RFID tag 10 is fixed in the region of the pivot joint of two arms 112, 114 of the instrument 110 by means of a laser weld 116. At the same time, this sealingly closes the accommodating chamber of the RFID tag 10 and thus protects the RFID element within the RFID tag 10 against environmental influences.

Figure 5:
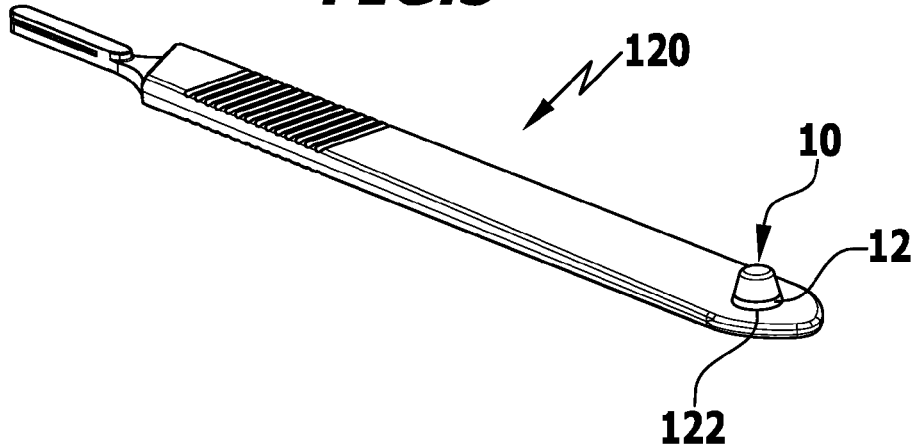
FIG. 5 shows a further surgical instrument having an RFID tag according to the invention as shown in FIG. 1A.

FIG. 5 likewise shows the use of an RFID tag 10 that is fixed on a scalpel holder 120. Again, the RFID tag 10 with its metal holder 12 has been sealingly connected to the surface of the surgical instrument 120 via a circumferential laser weld 122.

Figure 6:
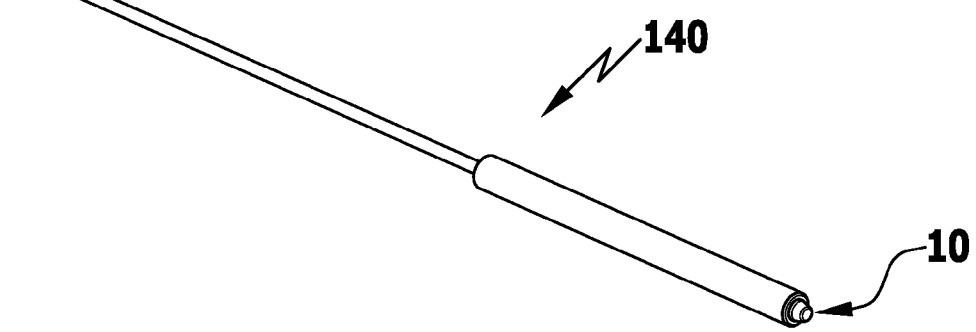
FIG. 6 shows a further surgical instrument having an RFID tag according to the invention as shown in FIG. 1A.

FIG. 6 shows the securing of an RFID tag 10 to a surgical instrument 140 that assumes the shape of a hook. It is shown here that the RFID tags of the present invention can be very small in size and can also be secured on very small surfaces in a reliable, i.e, sealing, manner.

FIG. 7 shows a clamp 160 in which, on the one hand, an RFID tag 10 is welded to a plane surface in the region of the pivot joint of two arms 162, 164. Moreover, on a ring 166 at the proximal end of the handle arm 162, a further RFID tag 60, as described in connection with FIG. 2C, is arranged which assists in facilitating the identification of the instrument 116 when this instrument is to be detected in a group with other instruments.

FIG. 8 shows the clamp 160 of FIG. 7, this time with two RFID tags 10 mounted on the upper and lower sides of the two handle arms 162, 164. The effect of the instrument 160 itself shadowing the antenna signal can thus be considerably reduced. The emission characteristic of the two RFID tags 10 is schematically illustrated in FIG. 8. The RFID tags can thus be read out essentially independently of the position of the instrument.

Lastly, FIG. 9 shows the clamp 160 equipped with two RFID tags 80', 80", as described in connection with FIGS. 3A and 3B. The RFID tags 80', 80" are arranged on the rings 166, 168 of the handle arms 162 and 164, respectively, the orientation of the RFID tags 80', 80" with their antennas being selected to be orthogonal to one another, as can easily be seen by the orientation of the surfaces 89', 89" relative to one another. The emission characteristic of the two RFID tags 80', 80" is also schematically shown in FIG. 9. Here, reading out the RFID tags is possible in any position or location of the instrument.

The invention claimed is:

1. An RFID tag for mounting on surgical instruments, comprising:
   a metal holder,
   a housing that is made of an electrically non-conductive or slightly conductive material having an accommodating chamber, and
   an RFID element with an antenna arranged in the accommodating chamber,
   wherein:
      the housing has a first end which is held on the metal holder,
      the accommodating chamber is formed to be spatially spaced apart from the first end of the housing, and
      the RFID element is positioned in the accommodating chamber in such a way that the antenna of the RFID element is spatially arranged substantially outside of the metal holder.

2. The RFID tag according to claim 1, wherein the housing is made of a plastics material or a ceramic material.

3. The RFID tag according to claim 1, wherein the housing has an opening on one side, the opening forming an access to the accommodating chamber.

4. The RFID tag according to claim 3, wherein the first end comprises the opening which forms the access to the accommodating chamber.

5. The RFID tag according to claim 4, wherein the RFID element is arranged in the accommodating chamber with the antenna facing away from the metal holder.

6. The RFID tag according to claim 1, wherein the accommodating chamber is closable by a closure element.

7. The RFID tag according to claim 6, wherein the closure element is glued or welded to the housing.

8. The RFID tag of claim 7, wherein the closure element is welded to the housing by means of ultrasound.

9. The RFID tag according to claim 1, wherein the housing is injection-molded onto the metal holder.

10. The RFID tag according to claim 1, wherein the metal holder is injection-molded onto the housing.

11. The RFID tag according to claim 1, wherein the housing is held on the metal holder in at least one of a form-fit and a positive-fit manner.

12. The RFID tag of claim 11, wherein the housing is held on the metal holder by a press fit.

13. The RFID tag according to claim 1, wherein the RFID element is fixed in the accommodating chamber by means of an adhesive.

14. The RFID tag of claim 13, wherein the adhesive is based on a silicone material.

15. An RFID tag for mounting on surgical instruments, comprising:
   a metal holder,
   a housing that is made of an electrically non-conductive or slightly conductive material having an accommodating chamber, and
   an RFID element with an antenna arranged in the accommodating chamber,
   wherein:
      the housing has a first end which is held on the metal holder,
      the accommodating chamber is formed to be spatially spaced apart from the first end of the housing,
      the RFID element is positioned in the accommodating chamber in such a way that the antenna of the RFID element is spatially arranged substantially outside of the metal holder, and
      the housing has a substantially planar surface region, a plane of the substantially planar surface region having a predefined orientation relative to the antenna of the RFID element.

16. An RFID tag for mounting on surgical instruments, comprising:
   a metal holder,
   a housing that is made of an electrically non-conductive or slightly conductive material having an accommodating chamber, and
   two RFID elements, each with a respective antenna, arranged in the accommodating chamber,
   wherein:
      the housing has a first end which is held on the metal holder,
      the accommodating chamber is formed to be spatially spaced apart from the first end of the housing,
      the RFID element is positioned in the accommodating chamber in such a way that the antenna of the RFID element is spatially arranged substantially outside of the metal holder, and
      the two RFID elements are oriented relative to one another in such a manner that planes of the respective antennas form an angle of approximately 70° to approximately 110° with one another.

17. The RFID tag of claim 16, wherein the planes of the antennas form an angle of approximately 90° with one another.

18. A surgical instrument equipped with an RFID tag, the RFID tag comprising:
   a metal holder secured to a surface of the surgical instrument,
   a housing that is made of an electrically non-conductive or slightly conductive material having an accommodating chamber, and
   an RFID element with an antenna arranged in the accommodating chamber,
   wherein:
      the housing has a first end which is held on the metal holder,
      the accommodating chamber is formed to be spatially spaced apart from the first end of the housing, and
      the RFID element is positioned in the accommodating chamber in such a way that the antenna of the RFID element is spatially arranged substantially outside of the metal holder.

19. The surgical instrument according to claim 18, wherein the metal holder is welded to the instrument.

20. The surgical instrument according to claim 19, wherein the metal holder is welded to the instrument by means of laser welding.

21. The surgical instrument according to claim 18, wherein two or more RFID tags are mounted on the instrument.

22. A surgical instrument equipped with two or more RFID tags, each of the two or more RFID tags comprising:
   a metal holder secured to a surface of the surgical instrument,
   a housing that is made of an electrically non-conductive or slightly conductive material having an accommodating chamber, and
   an RFID element with an antenna arranged in the accommodating chamber,
   wherein:
      the housing has a first end which is held on the metal holder,
      the accommodating chamber is formed to be spatially spaced apart from the first end of the housing, the RFID element is positioned in the accommodating chamber in such a way that the antenna of the RFID element is spatially arranged substantially outside of the metal holder, and the two or more RFID tags are arranged on the instrument in such a manner that the antennas of the respective RFID elements of the two or more RFID tags are aligned in different planes.

23. The surgical instrument of claim 22, wherein the planes form an angle of approximately 70° to approximately 110° with one another.

24. The surgical instrument of claim 23, wherein the planes form an angle of approximately 90° with one another.

* * * * *

UNITED STATES PATENT AND TRADEMARK OFFICE
CERTIFICATE OF CORRECTION

| | |
|---|---|
| PATENT NO. | : 9,033,251 B2 |
| APPLICATION NO. | : 14/141592 |
| DATED | : May 19, 2015 |
| INVENTOR(S) | : Weisshaupt et al. |

It is certified that error appears in the above-identified patent and that said Letters Patent is hereby corrected as shown below:

In the Claims:

Column 8, line 18-20: "the RFID element is positioned in the accommodating chamber in such a way that the antenna of the RFID element is spatially arranged substantially outside of"

should read:

-- the two RFID elements are positioned in the accommodating chamber in such a way that the antennas of the two RFID elements are spatially arranged substantially outside of --

Signed and Sealed this
Twenty-seventh Day of October, 2015

Michelle K. Lee
*Director of the United States Patent and Trademark Office*